United States Patent [19]

Kindel

[11] 4,272,049
[45] Jun. 9, 1981

[54] MOULD FOR MOULDING SPECIMEN BLOCKS TO BE CUT IN A MICROTOME OR AN ULTRAMICROTOME

[75] Inventor: Erik L. Kindel, Älvsjö, Sweden

[73] Assignee: LKB-Produkter AB, Bromma, Sweden

[21] Appl. No.: 48,363

[22] Filed: Jun. 14, 1979

[30] Foreign Application Priority Data

Jun. 21, 1978 [SE] Sweden ................................ 7807073

[51] Int. Cl.³ ...................... B29C 17/14; B32B 31/18; C04B 41/44; G01N 1/06
[52] U.S. Cl. ............................................. 249/83; 83/915.5; 249/120; 249/127; 264/40.1; 264/139; 264/275; 425/173
[58] Field of Search .................... 249/83, 127, 120; 425/173; 83/915.5

[56] References Cited

U.S. PATENT DOCUMENTS

| | | | |
|---|---|---|---|
| 2,053,711 | 9/1936 | Glomb | 249/127 |
| 2,182,454 | 12/1939 | Sherman | 249/127 |
| 2,285,149 | 6/1942 | D'Arcey | 249/120 |
| 2,433,210 | 12/1947 | Gits | 249/127 |
| 2,469,067 | 5/1949 | Follin | 249/120 |
| 2,932,386 | 4/1960 | Ushkow | 249/127 |
| 2,955,044 | 10/1960 | Tupper | 249/127 |
| 2,996,762 | 8/1961 | McCormick | 264/238 |
| 3,261,600 | 7/1966 | Horn | 83/915.5 |
| 3,807,604 | 4/1974 | Schaffer et al. | 83/915.5 |
| 3,859,020 | 1/1975 | Rentz | 425/173 |
| 3,996,326 | 12/1976 | Schachet | 264/330 |
| 4,012,475 | 3/1977 | Kindel | 264/28 |
| 4,044,161 | 8/1977 | Tanara | 249/127 |
| 4,076,207 | 2/1978 | Austin | 249/127 |

Primary Examiner—John C. Bleutge
Assistant Examiner—A. H. Koeckert
Attorney, Agent, or Firm—Fisher, Christen & Sabol

[57] ABSTRACT

A mould to be used for making specimen blocks for embedding specimens to be sectioned by a microtome, or ultramicrotome, is made from a soft heat resistant plastic to provide a number of cavities having the desired shape for the blocks to be moulded, the walls of the lowermost portions of the cavities being thin enough to be deformable by upward pressure on the exterior of the mould to remove the finished blocks with their embedded specimens.

1 Claim, 3 Drawing Figures

MOULD FOR MOULDING SPECIMEN BLOCKS TO BE CUT IN A MICROTOME OR AN ULTRAMICROTOME

BACKGROUND OF THE INVENTION

The present invention refers to a mould for moulding specimen blocks to be cut in a microtome or an ultramicrotome.

FIELD OF THE INVENTION

When studying a sample in an electron microscope and in certain cases also in a light microscope the sample is cast in a specimen block usually consisting of a thermosetting resin, the specimen block thus obtained then being cut in an ultramicrotome or a microtome. The specimen block should then have a shape so as to make it possible to clutch it into the microtome or ultramicrotome and furthermore, the sample which is often a piece of tissue should be oriented in a suitable way in the block for the subsequent cutting. The conventional shape of a specimen block is usually a cylindrical part to be clutched into a sample holder in the microtome and a protruding part which could have the shape of a cone or a pyramid and which contains the tissue. The protruding part should thereby have a suitable shape for the knife trimming of the specimen block which is carried out in order to obtain the adequate conditions for the subsequent cutting.

DESCRIPTION OF THE PRIOR ART

As moulds for the specimen block usually gelatine capsules or polyethene moulds of a simple design made as single or multiple moulds are used. The gelatine capsules as well as the polyethene moulds have considerable disadvantages.

Thus, the gelatine capsule requires a special holder during the polymerisation of the resin of the specimen block, since this polymerisation takes place while heat is supplied. The holder should thereby maintain the capsules in a vertical position and permit air circulation, especially around the protruding part where the sample is located. The capsules could thus not be in contact with the bottom of for instance a heating cuboard. As embeddings of samples in blocks is usually made in quantities of several hundreds this requires a big number of holders which could only be used a limited number of times, since they are subject to overflow when filling the capsules. Furthermore, the loading of the holders is time consuming. A further disadvantage of using gelatine capsules is that the gelatine is removed by dissolution in hot water, which requires time and could affect the cutting properties of the block.

As a substitute for the gelatine capsules polyethene moulds are available for moulding specimen blocks whereby the bottom of the mould has the shape of a frustum of a cone or pyramid, which gives better or faster trimming facilities than the bottom shape obtained by using gelatine capsules. Such polyethene moulds are also available in a multiple design with several moulds whereby the use of a separate holder in the polymerisation has been eliminated, but on the other hand the bottoms of the cavities will be located directly on the support thus deteriorating the air circulation around the mould and gives rise to a heterogeneous polymerisation. Furthermore the polyethene moulds are removed by being cut with a razor blade which is time consuming and involves the risk of the operator to cut himself. Furthermore, these polyethene moulds are not transparent which makes the orientation of the sample in the block more difficult.

SUMMARY OF THE INVENTION

It is an object of the present invention to obtain a mould for moulding specimen blocks in which the above mentioned drawbacks are eliminated. The characteristics of the invention will appear from the claims attached to the specification.

BRIEF DESCRIPTION OF THE DRAWING

The invention will now be described in detail, reference being made to the attached drawing in which.

DESCRIPTION OF A PREFERRED EMBODIMENT OF THE INVENTION

Figure 1:
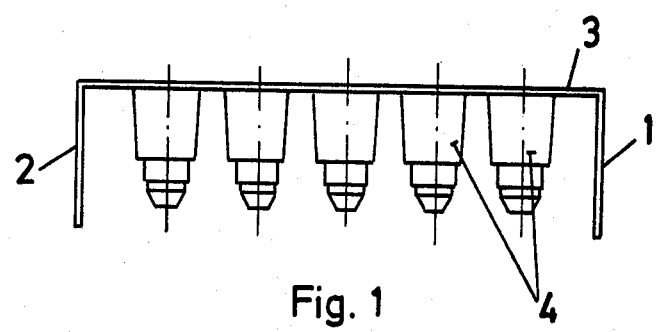
FIG. 1 is a side-view of a mould according to the invention.
Figure 2:
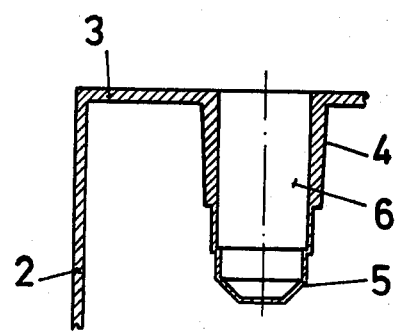
FIG. 2 is a cross-sectional view of an enlarged part of FIG. 1.
Figure 3:
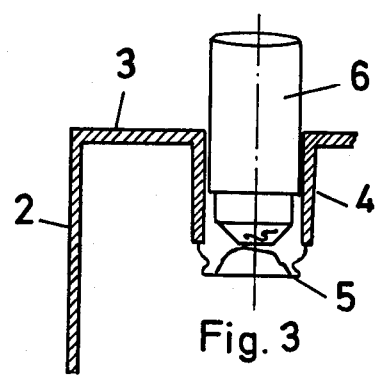
FIG. 3 shows the detail of FIG. 1 whereby a mould block has been pressed out of the mould.

In FIG. 1 which is a side view of a mould according to the invention, reference 3 denotes a horizontal plate carried by two side walls 1 and 2. The plate is provided with a number of cavities 4 open at their tops and having a shape which appears from the figure. The plate and the side walls and cavities is pressed or injection moulded in a heat resistent plastic. The shape of the cavities is shown in detail in FIG. 2 where reference 5 denotes the lower part of the mould in which part the samples are located, whereas reference 6 denotes the block as such. As appears from this figure the upper part of the cavitity has a cylindrical shape whereas its lower part in which the sample is located is designed in a suitable way for subsequent trimming and cutting. According to the invention the walls of the lower part 5 is so thin that it could easily be deformed when subject to a finger pressure. The part 5 is suitably transparent so that the location of the sample can be studied. FIG. 3 shows the deformation of the deformation zone 5 when removing the block 6 from the mould. In order to remove all blocks simultaneously two plates could preferably be used, the plate on the receiving side being provided with bores for the blocks. The use of a transparent part 5 also includes the possibility of having a marking strip moulded into the plastic block, the information of the strip being detected through the wall 5.

We claim:

1. A mould for moulding specimen blocks to be cut in a microtome or an ultramicrotome, characterized in that it comprises an elongated horizontal plate and two integrally moulded supporting side walls the plate and the side walls being made from a soft heat resistant plastic and the plate being provided with a number of integrally formed depending cavities of a substantially cylindrical upper internal shape corresponding to the desired shape of the specimen block, the plate, side walls and the major upper parts of the cavities having relatively thick walls and the bottom part of each cavity being provided with a thin-walled deformable substantially transparent zone so as to enable the moulded block to be pressed out of the mould by means of deforming the deformation zone, the vertical height of the side walls being greater than the extending depending length of the cavities to prevent contact of the cavities with a horizontal supporting surface.

* * * * *